United States Patent
Saito et al.

(10) Patent No.: US 9,290,841 B2
(45) Date of Patent: Mar. 22, 2016

(54) ORGANORUTHENIUM COMPOUND FOR CHEMICAL VAPOR DEPOSITION RAW MATERIAL AND PRODUCTION METHOD FOR THE ORGANORUTHENIUM COMPOUND

(75) Inventors: Masayuki Saito, Ibaraki (JP); Junichi Taniuchi, Ibaraki (JP); Hirofumi Nakagawa, Ibaraki (JP)

(73) Assignee: TANAKA KIKINZOKU KOGYO K.K., Tokyo (JP)

( * ) Notice: Subject to any disclaimer, the term of this patent is extended or adjusted under 35 U.S.C. 154(b) by 280 days.

(21) Appl. No.: 14/007,763

(22) PCT Filed: Jul. 24, 2012

(86) PCT No.: PCT/JP2012/068654
§ 371 (c)(1),
(2), (4) Date: Sep. 26, 2013

(87) PCT Pub. No.: WO2013/018577
PCT Pub. Date: Feb. 7, 2013

(65) Prior Publication Data
US 2014/0057050 A1    Feb. 27, 2014

(30) Foreign Application Priority Data
Aug. 3, 2011 (JP) .................................. 2011-170242

(51) Int. Cl.
| | |
|---|---|
| C07F 15/00 | (2006.01) |
| C23C 16/00 | (2006.01) |
| C23C 16/16 | (2006.01) |
| C23C 16/30 | (2006.01) |
| H01L 21/285 | (2006.01) |

(52) U.S. Cl.
CPC ............. *C23C 16/16* (2013.01); *C07F 15/0046* (2013.01); *C23C 16/30* (2013.01); *H01L 21/28556* (2013.01)

(58) Field of Classification Search
CPC ...... C07F 15/0046; C23C 16/16; C23C 16/30
USPC .......................................... 556/136; 427/252
See application file for complete search history.

(56) References Cited

U.S. PATENT DOCUMENTS
| | | |
|---|---|---|
| 3,446,591 A | 5/1969 | Piero Pino et al. |
| 2005/0090679 A1 | 4/2005 | Hirakoso et al. |
| 2007/0072401 A1 | 3/2007 | Suzuki |
| 2010/0116738 A1 | 5/2010 | Xia et al. |
| 2011/0027977 A1 | 2/2011 | Li |
| 2012/0055403 A1 | 3/2012 | Gomi et al. |

FOREIGN PATENT DOCUMENTS
| | | |
|---|---|---|
| EP | 1870159 A1 | 12/2007 |
| GB | 1160765 | 8/1969 |
| WO | 2006/109860 A1 | 10/2006 |
| WO | WO 2007/112394 A2 | 10/2007 |
| WO | WO 2007/112394 A3 | 10/2007 |
| WO | 2010/101191 A1 | 9/2010 |

OTHER PUBLICATIONS

EP12819564.1 European Search Report.
Banditelli, P. et al. "Decomposition Studies of Triruthenium Dodecacarbonyl and Triosmium Dodecacarbonyl." Thermochimica Acta, 1976, vol. 16, pp. 89-93.
Green, M.L. et al. "Chemical Vapor Deposition of Ruthenium and Ruthenium Dioxide Films." J. Electrochem. Soc., vol. 132 (No. 11), 1985, pp. 2677-2685.

*Primary Examiner* — Porfirio Nazario Gonzalez
(74) *Attorney, Agent, or Firm* — Roberts & Roberts, LLP

(57) ABSTRACT

The present invention is an organoruthenium compound for a chemical vapor deposition raw material, including dodecacarbonyl triruthenium represented by the following chemical formula, wherein the iron (Fe) concentration is 1 ppm or less. The DCR in the present invention can be produced by obtaining crude DCR by directly carbonylating ruthenium through allowing a ruthenium salt and carbon monoxide to react with each other and by purifying the crude DCR by a sublimation method. In the synthesis step, the concentration of Fe in the obtained crude DCR is preferably set at 10 ppm or less.

[Formula 1]

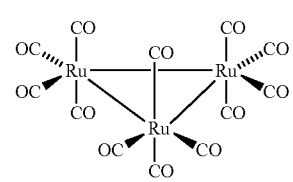

20 Claims, No Drawings

ORGANORUTHENIUM COMPOUND FOR CHEMICAL VAPOR DEPOSITION RAW MATERIAL AND PRODUCTION METHOD FOR THE ORGANORUTHENIUM COMPOUND

BACKGROUND OF THE INVENTION

1. Technical Field

The present invention relates to an organoruthenium compound suitable as a raw material for producing a ruthenium thin film or a ruthenium compound thin film by a chemical vapor deposition method such as a CVD method.

2. Background Art

Ruthenium or a ruthenium compound is used as the thin film material for forming an underlayer of a copper wiring in a semiconductor. As a method for producing such thin films, a chemical vapor deposition method such as a CVD method (chemical vapor deposition method) or an ALD method (atomic layer deposition method) is applied.

As a raw material compound used in the chemical vapor deposition method, a large number of organoruthenium compounds have hitherto been known. Among the organoruthenium compounds, as one of the compounds for which practical application has been investigated, there is dodecacarbonyl triruthenium (hereinafter, referred to as DCR) (Non Patent Literature 1 and Patent Literature 1).

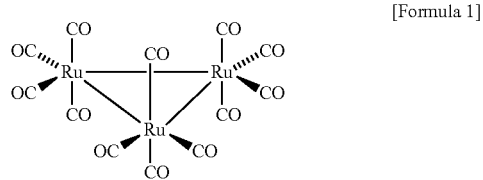

[Formula 1]

DCR is a substance having a melting point of 154 to 155° C. and being solid (orange crystal) at normal temperature. Usually, a raw material for chemical vapor deposition liquid at normal temperature is regarded as preferable from the viewpoint of, for example, the handleability in the vaporization of the raw material. However, in the case of DCR, the utilization thereof is expected from the following reasons: because of the simple molecular structure thereof constituted with Ru and CO and a fact that a film of DCR can be formed only by thermal decomposition without any use of reaction gas, DCR has an advantage such that DCR scarcely allows an impurity such as a hydrocarbon to remain in the thin film formed with DCR; and although DCR is a solid raw material, the regulation of the specification of the raw material vessel or an appropriate process control allows the production efficiency of the DCR thin film to be free from adverse effects. In the production of the ruthenium thin film by using DCR, solid DCR is appropriately disposed in a raw material vessel, and while the solid DCR is being heated, the solid DCR is introduced, together with a reaction gas (such as hydrogen or oxygen), into a reaction chamber for causing a reaction and forming a film.

PRIOR ART DOCUMENTS

Patent Document

Patent Document 1: GB1160765

Non Patent Document

Non Patent Document 1: M. L. Green et al., J. Electrochem. Soc., Vol. 132 (No. 11), 1985, pp. 2677-2685.

SUMMARY OF THE INVENTION

Problems to be Solved by the Invention

As described above, DCR can be said to be a raw material compound enabling the production of a satisfactory ruthenium thin film with an appropriate configuration of equipment. In the meantime, demand for improvements toward practical application of DCR is under way. Examples of the demand for the improvement of DCR include, first of all, the achievement of high quality of the formed thin film of DCR. Such a demand for improvement may be an improvement item to be quoted for any raw material compound; however, a ruthenium film using DCR undergoes, with an extremely low probability, the occurrence of film formation failure such as disconnection, and hence improvement for ensuring high product yield is demanded.

Among others, an improvement demand specific to DCR is associated with occasional occurrence of a phenomenon that ignition occurs when the raw material vessel is opened after the production of the thin film. The ignition phenomenon is not caused by the raw material compound before the use, but is based on the ignitability possessed by the remaining fraction of the raw material compound once used. Such an ignition phenomenon impairs the work safety and leads to the increase of the costs for equipment security, and hence it is preferable to prevent the ignition phenomenon.

The present invention was made in view of the foregoing problems, and provides an organoruthenium compound including DCR, hardly causing ignition phenomenon, ensuring the safety, and being capable of forming a high-quality ruthenium thin film or a high-quality ruthenium compound thin film.

Means for Solving the Problems

The present inventors studied the states of the raw material compound before and after the film formation reaction on the basis of DCR heretofore available, for the purpose of solving the foregoing problems. Consequently, it has been verified that in the case where the film formation is conducted with use of conventional DCR, even when the film formation is conducted until the raw material compound is sublimed completely, the residue remains in the raw material vessel. The residue after the sublimation of DCR is regarded as the impurity in the raw material compound on the basis of a simple consideration; however, in this stage of the investigation, it is not advisable to exclude the consideration about the compound produced by heating from the impurity or the possibility of the transformation of DCR. Accordingly, the present inventors performed a detailed component analysis of the conventional DCR, and at the same time, investigated and examined the items such as the production step of the conventional DCR and the state of the raw material compound during the thin film formation (during vaporization), and studied the relation between the factor generating the residue and the ignition phenomenon.

Consequently, the present inventors first have found that the conventional DCR contains impurities in a content of a few tens to 100 ppm, and in particular, contains iron (Fe) in a larger amount. Thus, the present inventors have considered that in the case where iron is a main factor of the residue, the factor for the ignition phenomenon resides in the residue. Specifically, it is possible to assume that iron is mixed in the course of the synthesis of DCR, and the mixing iron produces pentacarbonyl iron ($Fe(CO)_5$). Pentacarbonyl iron is a substance which decomposes by light into spontaneously ignitable carbonyl iron ($Fe_2(CO)_9$) and carbon monoxide, and probably the light at the time of opening the raw material vessel causes the decomposition concerned, and thus the ignition phenomenon occurs. The phenomenat that DCR at the time of synthesis does not ignite but DCR after use ignites are probably ascribable to the conditions that DCR at the time of production is embedded in the DCR crystal, but after the use, pentacarbonyl iron is concentrated on the DCR crystal surface so as to be easily brought into contact with air.

From the results of the foregoing investigation, the present inventors have obtained a view that the DCR as the raw material for the ruthenium film formation needs the regulation of the iron concentration.

The present invention solving the foregoing problems is an organoruthenium compound for a chemical vapor deposition raw material, including dodecacarbonyl triruthenium (DCR) represented by the following chemical formula, wherein the iron (Fe) concentration is 1 ppm or less.

[Formula 1]

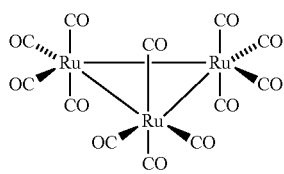

As described above, the organoruthenium compound for a chemical vapor deposition raw material according to the present invention is regulated in the iron concentration. The upper limit of the iron concentration set at 1 ppm is the upper limit value for suppressing the occurrence of the residue to be a factor for causing the ignition phenomenon and for ensuring the quality of the ruthenium thin film. More preferably, the concentration of iron is reduced to 0.5 ppm or less. This is for the purpose of more certainly suppressing the occurrence of the residue.

As the organoruthenium compound for a chemical vapor deposition raw material, other impurities are also preferably reduced. Examples of the impurities to be regulated include: lithium (Li), sodium (Na), magnesium (Mg), aluminum (Al), calcium (Ca), potassium (K), titanium (Ti), vanadium (V), chromium (Cr), manganese (Mn), cobalt (Co), nickel (Ni), copper (Cu), zinc (Zn), strontium (Sr), yttrium (Y), molybdenum (Mo), iridium (Ir), platinum (Pt), gold (Au), lead (Pb), thorium (Th) and uranium (U). Any of the concentrations of the impurity elements other than iron is preferably 1 ppm or less. More preferably, the concentrations of the impurity elements other than iron are also set at 0.5 ppm or less. The sum of the concentrations of the forgoing impurity elements inclusive of iron is particularly preferably 1 ppm or less.

A method for forming a thin film, by using as the raw material compound the organoruthenium compound according to the present invention, is the same as a common chemical vapor deposition method (a CVD method or an ALD method). Specifically, the raw material compound is vaporized to prepare a reaction gas, the reaction gas is heated while the reaction gas is being introduced to the surface of a substrate, and thus, ruthenium or a ruthenium compound is deposited.

Next, the method for producing DCR, which is the organoruthenium compound according to the present invention, is described. The method for producing DCR according to the present invention includes: a synthesis step of allowing a ruthenium salt and carbon monoxide to react with each other in a solvent and a purification step of purifying the crude DCR obtained in the synthesis step by a sublimation method.

The method according to the present invention includes the two steps, namely, the step of synthesizing DCR and the step of purifying DCR. Here, the step of synthesizing DCR is based on a method of directly carbonylating a ruthenium salt with carbon monoxide (hereinafter, referred to as the direct method). As the method for producing DCR, in addition to the direct method, for example, a method is known in which a ruthenium salt is used as a raw material, the ruthenium salt is allowed to react with an acetylacetonate salt to yield ruthenium acetylacetonate, the ruthenium acetylacetonate is used as an intermediate and the intermediate is carbonylated; however, the method going through an intermediate is increased in the number of steps and in the number of the chances of impurity mixing, and hence, a direct method is adopted.

In the present invention, the conditions for the synthesis of DCR by the direct method are such that the reaction pressure is set at 3.0 to 6.5 MPa, the reaction temperature is set at 75 to 125° C., and the reaction time is set at 8 to 20 hours. Among these reaction conditions, in particular the reaction pressure is a condition requiring care. The reaction pressure takes account of the corrosion of the materials constituting the reaction vessel by carbon monoxide. Specifically, the corrosivity of carbon monoxide is usually regarded to be of a negligible degree; however, carbon monoxide tends to react with metals, which are the materials for the high pressure vessel, such as iron, nickel and chromium under a high pressure to produce metal carbonyl compounds. An industrial DCR synthesis apparatus is assumed to use a high pressure vessel made of a steel such as a stainless steel, and hence, the increase of the reaction pressure involves an apprehension that iron contamination due to the apparatus corrosion may occur. From such a viewpoint, the present invention sets the reaction pressure falling within the foregoing range in which the carbonylation reaction can be made to proceed and at the same time, can prevent the corrosion due to carbon monoxide. The foregoing conditions are set for the reaction temperature and the reaction time because the deviations of the reaction temperature and the reaction time from the foregoing conditions cause a drastic reduction of the yield.

The ruthenium salt as the raw material in the synthesis step is preferably ruthenium chloride, ruthenium oxide, ruthenium nitrate, hexaammine ruthenium chloride or ruthenium acetate. The ruthenium salts are commercially available substances, and can be easily obtained. In particular, ruthenium chloride is preferable. As a matter of course, a high-purity raw material is preferable. Ruthenium acetylacetonate (tris(acetylacetonato)ruthenium (III)) is also commercially available, and hence, such a commercially available product can be used as a starting material if the purity thereof is high.

In the synthesis of an organometallic compound such as DCR, an auxiliary metal having catalysis is frequently used; however, the application of such an auxiliary metal becomes a factor for contamination of an impurity, and hence the addition of an auxiliary metal is unnecessary.

The foregoing step of synthesizing DCR is a step reduced itself in the content of each of impurities (in particular, iron). The DCR in the synthesis step is referred to as the crude DCR; however, the iron concentration in the crude DCR is preferably made to be 10 ppm or less.

The purification step is a step for further reducing the iron concentration in the crude DCR. The purification step is based on a sublimation method. In a common purification of a compound, in addition to a sublimation method, for example, distillation, recrystallization and column chromatography methods are known: however, a sublimation method is most appropriate for DCR because DCR is solid and high in melting point, low in solubility in solvents, and additionally, separation from the contaminating impurities cannot be achieved, for example, by recrystallization.

The purification conditions by the sublimation method are such that the degree of vacuum is set at 50 Pa or less, the heating temperature is set at 80° C. to 110° C. and the cooling temperature is set at 20° C. or lower. This is because: when the degree of vacuum exceeds 50 Pa, the sublimation rate is decreased and the sublimation rate is drastically extended; and when the heating temperature is lower than 80° C., the sublimation time is made drastically slow, and when the heating temperature exceeds 110° C., the sublimation rate is increased, but the partial thermal decomposition of DCR possibly occurs and consequently the yield is drastically reduced.

In the present invention, it is essential to purify the synthesized crude DCR by a sublimation method; however, the DCR having been subjected to the purification by the sublimation method may also be again purified by applying thereto another purification method (such as a recrystallization or column chromatography method). For example, after the purification has been performed by a sublimation method, the DCR may be purified again by a recrystallization method. The iron concentration itself is sufficiently reduced by the purification based on the sublimation method; however, when the organic matter or the like accompanying the DCR in a trace amount at the time of sublimation is sufficiently removed, a repurification may be performed by recrystallization.

Advantageous Effects of Invention

As described above, the organoruthenium compound according to the present invention includes the DCR having a reduced iron concentration. The present invention does not generate the residue after use and suppresses the ignition phenomenon due to the residue. Thus, the safety of the thin film production is ensured and the workability becomes satisfactory.

When the iron as an impurity is vaporized accompanying DCR at the time of vaporization of the raw material, the iron possibly contaminate the ruthenium thin film, and such contaminating iron may become a factor for disconnection or degradation of electric properties. Accordingly, the organoruthenium compound according to the present invention, in which the iron concentration is limited, enables the production of a high-quality ruthenium thin film.

DETAILED DESCRIPTION OF THE PREFERRED EMBODIMENTS

First Embodiment: In 300 mL of methanol as a solvent, 25.4 g of ruthenium chloride was dissolved. The resulting solution was placed in a 1-L capacity autoclave (made of steel), and carbon monoxide was filled in the autoclave until the reaction pressure reached 6.5 MPa. Then, the reaction solution was heated and allowed to react at 125° C. for 8 hours. After the synthesis reaction, the reaction solution was cooled and filtered to take out the filtered-off product, and thus 15.4 g of an orange DCR crude crystal was obtained. The concentration of iron of the synthesized DCR crude crystal was measured with ICP and was found to be 7 ppm.

The DCR crude crystal obtained by the synthesis step was purified by a sublimation method. In the purification step, the DCR crude crystal was placed in a pear-shaped sublimator and sublimed under the following conditions.

Degree of vacuum: 1 Pa
Temperature: 95° C.
Sublimation time: 6 hours
Cooling water temperature: 8° C.

The DCR crystal sampled in a cooling section after the completion of the sublimation was subjected to a measurement of impurity elements with an ICP-MS and the following results were obtained.

TABLE 1

Unit: ppm

| | Element | | | | | | | | | |
|---|---|---|---|---|---|---|---|---|---|---|
| | Fe | Li | Na | Mg | Al | Ca | K | Ti | V | Cr |
| Concentration | 0.5 | <0.1 | <0.1 | <0.1 | <0.1 | <0.1 | <0.1 | <0.1 | <0.1 | <0.1 |
| | Element | | | | | | | | | |
| | Mn | Co | Ni | Cu | Zn | Sr | Y | Mo | Ir | Pt |
| Concentration | <0.1 | <0.1 | <0.1 | <0.1 | <0.1 | <0.1 | <0.1 | <0.1 | <0.1 | <0.1 |
| | Element | | | | | | | | | |
| | Au | Pb | Th | U | | | | | | |
| Concentration | <0.1 | <0.1 | <0.1 | <0.1 | | | | | | |

*The lower limit of the quantitative determination of each of the elements is 0.1 ppm.

COMPARATIVE EXAMPLE

Here, DCR was produced by adopting, as a conventional method for producing DCR, a method by way of ruthenium acetylacetonate. In 600 mL of methanol, 15 g of ruthenium chloride and 22 g of sodium acetylacetonate were dissolved. The solution was placed in an autoclave (made of a steel) and the autoclave was increased in pressure to 12 MPa with a carbon monoxide:hydrogen (molar ratio: 3:1) mixed gas. Then, the solution was allowed to react at 160° C. for 4 hours.

After the synthesis reaction, the reaction solution was purified by recrystallization. The reaction solution was cooled and filtered, and the filtered-off product was placed in 1000 mL of benzene and completely dissolved by heating. Then, the solution was allowed to stand in a refrigerator set at 0° C. After 12 hours, the precipitated crystal was filtered off, and 9.4 g of an orange DCR crystal was obtained. The synthesized DCR crystal was subject to a measurement of the concentrations of the impurities with an ICP-MS, and the following results were obtained.

TABLE 2

Unit: ppm

| | | | | | Element | | | | | |
|---|---|---|---|---|---|---|---|---|---|---|
| | Fe | Li | Na | Mg | Al | Ca | K | Ti | V | Cr |
| Concentration | 120 | <0.1 | 2 | <0.1 | <0.1 | <0.1 | <0.1 | <0.1 | <0.1 | 27 |

| | | | | | Element | | | | | |
|---|---|---|---|---|---|---|---|---|---|---|
| | Mn | Co | Ni | Cu | Zn | Sr | Y | Mo | Ir | Pt |
| Concentration | <0.1 | <0.1 | 10 | <0.1 | <0.1 | <0.1 | <0.1 | <0.1 | <0.1 | <0.1 |

| | Element | | | |
|---|---|---|---|---|
| | Au | Pb | Th | U |
| Concentration | <0.1 | <0.1 | <0.1 | <0.1 |

*The lower limit of the quantitative determination of each of the elements is 0.1 ppm.

From a comparison of foregoing First Embodiment and Comparative Example, First Embodiment in which a ruthenium compound was directly carbonylated while the reaction pressure was being regulated was low in the Fe concentration of the crude DCR, and the carbonylation combined with a purification based on a sublimation method allows the Fe concentration to be 1 ppm or less. On the other hand, in Comparative Example, the Fe concentration is fairly higher than 120 ppm, even in consideration of the purification by a recrystallization method. This may be ascribable to the factors such that although Comparative Example adopted ruthenium chloride in the same manner as in First Embodiment, Comparative Example goes through ruthenium acetylacetonate, and hence the number of the steps are larger and correspondingly the possibility of impurity contamination is high, and the reaction pressure of the carbonylation of ruthenium acetylacetonate is relatively high and the contamination of iron from the reaction vessel is made to easily occur.

Second Embodiment: With use of the DCR produced in each of First Embodiment and Comparative Example, a ruthenium thin film was prepared by a CVD method. In a solid raw material vessel, 10 g of DCR was enclosed, and the film formation conditions were such that the heating temperature in the raw material vessel was set at 80° C., and the carrier gas was carbon monoxide and the reaction gas was hydrogen. The film formation test was performed five times, the occurrence or nonoccurrence of ignition when the raw material vessel was opened after the film formation, and further the amount of the residue in the raw material vessel were evaluated. The results thus obtained are shown in Table 3. In this test, the crude DCR crystal of First Embodiment, not yet subjected to the purification step was also used as a raw material and evaluated.

TABLE 3

| | Test No. | Ignition | Residue amount |
|---|---|---|---|
| First Embodiment (Fe = 0.5 ppm) | 1 | Not occurred | 0 g |
| | 2 | Not occurred | 0 g |
| | 3 | Not occurred | 0 g |
| | 4 | Not occurred | 0 g |
| | 5 | Not occurred | 0 g |
| Reference Example (No purification) (Fe = 7 ppm) | 1 | Not occurred | 0.057 g |
| | 2 | Not occurred | 0.024 g |
| | 3 | Not occurred | 0.013 g |
| | 4 | Occurred | —* |
| | 5 | Not occurred | 0.037 g |

TABLE 3-continued

| | Test No. | Ignition | Residue amount |
|---|---|---|---|
| Comparative Example (Fe = 120 ppm) | 1 | Occurred | —* |
| | 2 | Not occurred | 0.129 g |
| | 3 | Not occurred | 0.237 g |
| | 4 | Occurred | —* |
| | 5 | Occurred | —* |

*The residue amount was unmeasurable when ignition occurred.

As shown in Table 3, Comparative Example having an iron concentration of 120 ppm showed large residue amounts and showed the ignition phenomenon in three tests out of five tests. On the contrary, First Embodiment showed no residue and resulted in no observation of the ignition phenomenon. The crude DCR crystal (Reference Example) subjected to no purification step showed results better than the results of Comparative Example, but is inferior to First Embodiment subjected to a purification step. Accordingly, it can be verified that a thorough reduction of the iron concentration is necessary.

Third Embodiment: On the basis of the synthesis step of DCR in First Embodiment, the reaction conditions of the synthesis reaction (carbonylation) were investigated. Here, DCR (crude DCR) was synthesized by varying the reaction pressure, the reaction temperature and the reaction time, and the yield and the Fe concentration were evaluated. The other reaction conditions (raw material, solvent) were the same as in First Embodiment. The results thus obtained are shown in Table 4.

TABLE 4

| | Reaction conditions | | | | |
|---|---|---|---|---|---|
| Test No. | Reaction pressure | Reaction temperature | Reaction time | Yield | Fe concentration |
| 1 (First Embodiment) | 6.5 MPa | 125° C. | 8 Hr | 77.7% | 7 ppm |
| 2 | 3.0 MPa | 125° C. | 8 Hr | 46.2% | 3 ppm |
| 3 | 6.5 MPa | 60° C. | 8 Hr | 62.5% | 5 ppm |
| 4 | 6.5 MPa | 125° C. | 17 Hr | 70.0% | 8 ppm |

From Table 4, the lowering of the reaction pressure will be effective for the reduction of the Fe concentration. The reaction temperature also shows a similar tendency. However, the lowering of these conditions will simultaneously lower the yield. Accordingly, it will be preferable that the conditions are set in consideration of the fact that the crude DCR after the synthesis reaction must be subjected to the purification (sublimation) step, and in consideration of the balance between the yield and the purity.

Fourth Embodiment: Here, on the basis of the production process of the DCR in First Embodiment, the conditions of the purification step (sublimation step) were investigated. The crude DCR (Fe concentration: 7 ppm) synthesized in First Embodiment was purified by varying the degree of vacuum in the sublimation step and the sublimation temperature. The other conditions (sublimation time, cooling temperature) were the same as in First Embodiment. The results thus obtained are shown in Table 5.

TABLE 5

| Test No. | Purification conditions | | Fe concentration |
|---|---|---|---|
| | Degree of vacuum | Sublimation temperature | |
| 5 (First Embodiment) | 1 Pa | 95° C. | 0.5 ppm |
| 6 | 50 Pa | 80° C. | 0.2 ppm |
| 7 | 1 Pa | 110° C. | 0.3 ppm |

From Table 5, it has been verified that any set of purification conditions results in a preferable DCR having a Fe concentration of 0.5 ppm or less.

Industrial Applicability

The organoruthenium compound including DCR, according to the present invention has a reduced Fe concentration and enables the production of a high-quality ruthenium thin film. The organoruthenium compound including DCR, according to the present invention also generates no residue after use, suppresses the ignition phenomenon caused by the residue, and promotes the applicability of DCR, the applicability having involved handling difficulty due to ignition phenomenon.

What is claimed is:

1. An organoruthenium compound for a chemical vapor deposition raw material, comprising dodecacarbonyl triruthenium represented by the following chemical formula,

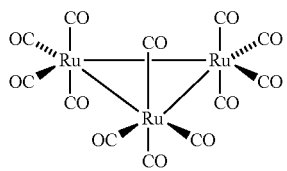

[Formula 1]

wherein the concentration of iron is 1 ppm or less.

2. The organoruthenium compound for a chemical vapor deposition raw material, according to claim 1, wherein further the concentration of each of all the following elements is 1 ppm or less: lithium, sodium, magnesium, aluminum, calcium, potassium, titanium, vanadium, chromium, manganese, cobalt, nickel, copper, zinc, strontium, yttrium, molybdenum, iridium platinum gold, lead, thorium and uranium.

3. The organoruthenium compound for chemical vapor deposition raw material, according to claim 1, wherein the sum of the concentrations of the following elements is 1 ppm or less: iron, lithium, sodium, magnesium, aluminum, calcium, potassium, titanium, vanadium, chromium, manganese, cobalt, nickel, copper, zinc, strontium, yttrium, molybdenum, iridium, platinum, gold, lead, thorium and uranium.

4. A chemical vapor deposition method for forming a ruthenium thin film or a ruthenium compound thin film by vaporizing an organoruthenium compound to be a raw material compound to prepare a reaction gas and by heating the reaction gas while the reaction gas is being introduced to the surface of a substrate, wherein as the organoruthenium compound, the organoruthenium compound defined in claim 1 is used.

5. A method for producing the organoruthenium compound for a chemical vapor deposition raw material, defined in claim 1, comprising: a synthesis step of obtaining a crude dodecacarbonyl triruthenium by directly carbonylating ruthenium through allowing a ruthenium salt and carbon monoxide to react with each other in a solvent and a purification step of purifying the crude dodecacarbonyl triruthenium obtained in the synthesis step by a sublimation method; wherein the synthesis step has reaction conditions such that a reaction pressure is 3.0 to 6.5 MPa, a reaction temperature is 75 to 125° C. and the reaction time is 8 to 20 hours; and the purification step has conditions such that a degree of vacuum is 50 Pa or less, a heating temperature is 80° C. to 110° C. and a cooling temperature is 20° C. or lower.

6. The method for producing the organoruthenium compound for a chemical vapor deposition raw material, according to claim 5, wherein the Fe concentration in the crude dodecacarbonyl triruthenium obtained by the synthesis step is 10 ppm or less.

7. The method for producing the organoruthenium compound for a chemical vapor deposition raw material, according to claim 5, wherein after the purification step by the sublimation method, dodecacarbonyl triruthenium is further purified by a recrystallization method.

8. The organoruthenium compound for chemical vapor deposition raw material, according to claim 2, wherein the sum of the concentrations of the following elements is 1 ppm or less: iron, lithium, sodium, magnesium, aluminum, calcium, potassium, titanium, vanadium, chromium, manganese, cobalt, nickel, copper, zinc, strontium, yttrium, molybdenum, iridium, platinum, gold, lead, thorium and uranium.

9. A chemical vapor deposition method for forming a ruthenium thin film or a ruthenium compound thin film by vaporizing an organoruthenium compound to be a raw material compound to prepare a reaction gas and by heating the reaction gas while the reaction gas is being introduced to the surface of a substrate, wherein as the organoruthenium compound, the organoruthenium compound defined in claim 2 is used.

10. A chemical vapor deposition method for forming a ruthenium thin film or a ruthenium compound thin film by vaporizing an organoruthenium compound to be a raw material compound to prepare a reaction gas and by heating the reaction gas while the reaction gas is being introduced to the surface of a substrate, wherein as the organoruthenium compound, the organoruthenium compound defined in claim 3 is used.

11. A chemical vapor deposition method for forming a ruthenium thin film or a ruthenium compound thin film by vaporizing an organoruthenium compound to be a raw material compound to prepare a reaction gas and by heating the reaction gas while the reaction gas is being introduced to the surface of a substrate, wherein as the organoruthenium compound, the organoruthenium compound defined in claim 8 is used.

12. A method for producing the organoruthenium compound for a chemical vapor deposition raw material, defined in claim 2, comprising: a synthesis step of obtaining a crude dodecacarbonyl triruthenium by directly carbonylating ruthenium through allowing a ruthenium salt and carbon monoxide to react with each other in a solvent and a purification step of purifying the crude dodecacarbonyl triruthenium obtained in the synthesis step by a sublimation method; wherein the synthesis step has reaction conditions such that a reaction pressure is 3.0 to 6.5 MPa, a reaction temperature is 75 to 125° C. and the reaction time is 8 to 20 hours; and the purification step has conditions such that a degree of vacuum is 50 Pa or less, a heating temperature is 80° C. to 110° C. and a cooling temperature is 20° C. or lower.

13. A method for producing the organoruthenium compound for a chemical vapor deposition raw material, defined in claim 3, comprising: a synthesis step of obtaining a crude dodecacarbonyl triruthenium by directly carbonylating ruthenium through allowing a ruthenium salt and carbon monoxide to react with each other in a solvent and a purification step of purifying the crude dodecacarbonyl triruthenium obtained in the synthesis step by a sublimation method; wherein the synthesis step has reaction conditions such that a reaction pressure is 3.0 to 6.5 MPa, a reaction temperature is 75 to 125° C. and the reaction time is 8 to 20 hours; and the purification step has conditions such that a degree of vacuum is 50 Pa or less, a heating temperature is 80° C. to 110° C. and a cooling temperature is 20° C. or lower.

14. A method for producing the organoruthenium compound for a chemical vapor deposition raw material, defined in claim 8, comprising: a synthesis step of obtaining a crude dodecacarbonyl triruthenium by directly carbonylating ruthenium through allowing a ruthenium salt and carbon monoxide to react with each other in a solvent and a purification step of purifying the crude dodecacarbonyl triruthenium obtained in the synthesis step by a sublimation method; wherein the synthesis step has reaction conditions such that a reaction pressure is 3.0 to 6.5 MPa, a reaction temperature is 75 to 125° C. and the reaction time is 8 to 20 hours; and the purification step has conditions such that a degree of vacuum is 50 Pa or less, a heating temperature is 80° C. to 110° C. and a cooling temperature is 20° C. or lower.

15. The method for producing the organoruthenium compound for a chemical vapor deposition raw material, according to claim 12, wherein the Fe concentration in the crude dodecacarbonyl triruthenium obtained by the synthesis step is 10 ppm or less.

16. The method for producing the organoruthenium compound for a chemical vapor deposition raw material, according to claim 13, wherein the Fe concentration in the crude dodecacarbonyl triruthenium obtained by the synthesis step is 10 ppm or less.

17. The method for producing the organoruthenium compound for a chemical vapor deposition raw material, according to claim 14, wherein the Fe concentration in the crude dodecacarbonyl triruthenium obtained by the synthesis step is 10 ppm or less.

18. The method for producing the organoruthenium compound for a chemical vapor deposition raw material, according to claim 12, wherein after the purification step by the sublimation method, dodecacarbonyl triruthenium is further purified by a recrystallization method.

19. The method for producing the organoruthenium compound for a chemical vapor deposition raw material, according to claim 13, wherein after the purification step by the sublimation method, dodecacarbonyl triruthenium is further purified by a recrystallization method.

20. The method for producing the organoruthenium compound for a chemical vapor deposition raw material, according to claim 14, wherein after the purification step by the sublimation method, dodecacarbonyl triruthenium is further purified by a recrystallization method.

\* \* \* \* \*